United States Patent
Lian et al.

(10) Patent No.: US 8,090,434 B2
(45) Date of Patent: Jan. 3, 2012

(54) DEVICE, METHOD AND COMPUTER-READABLE STORAGE MEDIUM FOR ENHANCED SENSE EVENT CLASSIFICATION IN IMPLANTABLE DEVICES BY MEANS OF MORPHOLOGY ANALYSIS

(75) Inventors: Jie Lian, Beaverton, OR (US); Garth Garner, Tigard, OR (US); Dirk Muessig, West Linn, OR (US)

(73) Assignee: Biotronik CRM Patent AG, Baar (CH)

( * ) Notice: Subject to any disclaimer, the term of this patent is extended or adjusted under 35 U.S.C. 154(b) by 459 days.

(21) Appl. No.: 12/368,328

(22) Filed: Feb. 10, 2009

(65) Prior Publication Data

US 2009/0240157 A1    Sep. 24, 2009

Related U.S. Application Data

(63) Continuation-in-part of application No. 12/210,381, filed on Sep. 15, 2008.

(60) Provisional application No. 61/037,334, filed on Mar. 18, 2008.

(51) Int. Cl.
*A61B 5/04* (2006.01)
(52) U.S. Cl. .......................... 600/515; 607/5
(58) Field of Classification Search .................. 600/515, 600/517; 607/5
See application file for complete search history.

(56) References Cited

U.S. PATENT DOCUMENTS

| | | | |
|---|---|---|---|
| 5,313,953 A * | 5/1994 | Yomtov et al. ............... | 600/508 |
| 5,447,519 A * | 9/1995 | Peterson ...................... | 607/5 |
| 6,393,316 B1 * | 5/2002 | Gillberg et al. ............... | 600/515 |
| 6,636,764 B1 | 10/2003 | Fain et al. | |
| 7,474,916 B2 * | 1/2009 | Gutierrez ..................... | 600/518 |
| 7,899,520 B2 * | 3/2011 | Lian et al. .................... | 600/509 |
| 2003/0181818 A1 | 9/2003 | Jaeho et al. | |
| 2006/0161069 A1 | 7/2006 | Dan | |
| 2006/0270937 A1 | 11/2006 | Koyrakh et al. | |

FOREIGN PATENT DOCUMENTS

| | | |
|---|---|---|
| DE | 10159296 | 6/2003 |
| EP | 1803485 | 7/2007 |
| EP | 1995685 | 11/2008 |
| WO | 2004105871 | 12/2004 |

OTHER PUBLICATIONS

European Search Report, dated Mar. 2, 2009, 8 pages.
Europea Search Report, dated Apr. 8, 2009, 10 pages.

(Continued)

*Primary Examiner* — Brian T Gedeon
(74) *Attorney, Agent, or Firm* — ARC IP Law, PC; Joseph J. Mayo

(57) ABSTRACT

An implantable cardiac device, e.g., a pacemaker, defibrillator, cardioverter or biventricular pacing device, that can sense cardiac electrical signals and accurately classify the sensed events. The device provides a template signal and a test signal originated from an electrogram. The device further transforms at least the test signal into a representation of the test signal for example in numerical format where the sample values of the test signal take the form of integers. The device further determines a correlation between the template and test signals, and classifies the sense events based on the correlation. The electrogram may be an intracardiac electrogram (IEGM), atrial electrogram (AEGM), ventricular electrogram (VEGM), surface electrocardiogram (ECG) or subcutaneous electrogram.

31 Claims, 6 Drawing Sheets

OTHER PUBLICATIONS

Wilkins J. "Correlation-based pattern recognition for implantable defibrillators," Proceedings: A Conference of the American Medical Informatics Association/AMIA Annual Fall Symposium, 1996, pp. 289-293.

Cebrian et al, "Optimization of three morphologic algorithms for arrhythmia discrimination in implantable cardioverter defibrillators," Computers in Cardiology, 2005, Lyon , France, Sep. 25-28, 2005, USA, IEEE, pp. 187-190.

Chang et al, "Comparison of similarity measures for clustering electrocardiogram complexes," Computers in Cardiology, Sep. 25-28, 2005, USA, IEEE, pp. 759-762.

* cited by examiner

DEVICE, METHOD AND COMPUTER-READABLE STORAGE MEDIUM FOR ENHANCED SENSE EVENT CLASSIFICATION IN IMPLANTABLE DEVICES BY MEANS OF MORPHOLOGY ANALYSIS

This application is a continuation in part U.S. patent application Ser. No. 12/210,381, filed 15 Sep. 2008, which claims the benefit of U.S. Provisional Patent Application Ser. No. 61/037,334, filed 18 Mar. 2008, the specifications of which are both hereby incorporated herein by reference.

BACKGROUND OF THE INVENTION

1. Field of the Invention

The present invention generally relates to implantable cardiac devices, including pacemakers, defibrillators and cardioverters, which stimulate cardiac tissue electrically to control the patient's heart rhythm. More particularly, the present invention relates to a method and apparatus for enhancing the sensing performance by means of morphological analysis of the intracardiac electrogram (IEGM) recorded by the implantable cardiac devices. The method disclosed in this invention is also applicable to devices and systems involving cardiac beat classification based on surface ECG analysis.

2. Description of the Related Art

Implantable cardiac devices, such as pacemakers, defibrillators and cardioverters, have been preferred therapy for treating various cardiac diseases, including bradyarrhythmia, tachyarrhythmia, heart failure, etc. Normal operation of these implantable cardiac devices requires reliable sensing of the cardiac electrical activity.

Currently, the sense detection is based on threshold crossing in all implantable pacemakers and ICDs. That is, a sense event is detected when the measured (and usually filtered) IEGM signal amplitude crosses above a predetermined sensing threshold. To minimize the problem of undersensing and oversensing, modern implantable cardiac devices can automatically adjust the sensing threshold (also known as sensitivity) so that it is adaptive to the IEGM signal amplitude.

However, the problems of oversensing and undersensing still exist, because the threshold crossing method alone could not resolve the sensing problems. Moreover, for sensed events, reliable event classification poses another challenge for the implant device.

Generally, the device sensed events could be classified into four classes: (1) normal intrinsic events, including normal atrial depolarization (P wave), and normal ventricular depolarization (QRS complex); (2) abnormal intrinsic depolarization, including ectopic atrial depolarization, ectopic ventricular depolarization, and retrograde P waves; (3) endogenous noise, including T waves, far-field R waves, far-field T waves, depolarization waveform double counting, and any other non-depolarization signal originating from within the heart; and (4) exogenous noise, including myopotentials, electromagnetic interference, lead failure artifact, in-channel and cross-channel pacing artifact, and any other signal originating from outside the heart.

For implantable cardiac devices, appropriate pacemaker timing and device diagnosis all depend on accurate event classifications. Particularly, the main task of event classification is to differentiate intrinsic events (classes 1 and 2) from non-intrinsic events (classes 3 and 4). Further classification of normal intrinsic events (class 1) from abnormal intrinsic events (class 2) is also desired.

Conventionally, the event classification in implantable cardiac devices is solely based on event timing information. As well known in the art, a plural of time intervals are defined (and mostly programmable) in the implantable cardiac device for event classification, such as atrial refractory period, ventricular refractory period, far-field blanking window, post-pace blanking window, and so on. A sense event outside the refractory period would be classified as an intrinsic event, whereas that inside the refractory period or a blanking window would be classified as a non-intrinsic event.

More complex algorithms were developed to improve the classification accuracy. For example, an atrial sense inside the atrial refractory period would be classified as an intrinsic P wave if it were followed by a normal ventricular sense event within a predefined time interval. On the other hand, atrial senses in the atrial refractory period following ventricular paces would be classified as retrograde P waves if the intervals from ventricular paces to the atrial senses are stable.

In another example, a ventricular sense outside the ventricular refractory period would be classified as a normal ventricular depolarization if it were preceded by an atrial event within a predefined time interval, or a ventricular extra-systole otherwise.

Yet in another example, when a device has no atrial sensing (e.g., in VVI mode), a ventricular sense outside the ventricular refractory period would be classified as a normal ventricular depolarization if the current ventricular coupling interval is not shorter than the average of preceding ventricular intervals by a predefined percentage (also called the prematurity index), otherwise a ventricular extra-systole is declared instead. Similar classification of normal atrial depolarization and atrial extra-systole can also be made.

All above event classification methods have the intrinsic limitation that only event timing information is utilized. As a result, the sensitivity and specificity of event classification is limited, and event misclassification is common in implantable cardiac devices. These limitations, on one hand, can potentially cause delay or withhold of appropriate therapies, and on the other hand, can potentially cause delivery of inappropriate therapies.

It is known that the morphology of the cardiac electric signal contains useful information for cardiac event classification. For example, the normal intrinsic cardiac depolarization usually has different morphology than that of the ectopic beat. Various pattern recognition techniques (e.g., neural network, fuzzy logic, etc.) have been developed for cardiac beat classification based on morphological analysis of the surface ECG signals. However, morphological analysis of IEGM is rarely used in the implantable cardiac devices for event classification, mainly due to the high complexity of these algorithms.

Generally, there are two different approaches for morphological analysis. In one approach, the morphology of the signal is characterized by a plural of metrics either directly measured from the signal (e.g., signal amplitude, width, area, slope, threshold crossing, peak polarity, etc.), or indirectly obtained from the transformed signal (e.g., Fourier transform, wavelet transform, symbolic and other nonlinear transforms, etc.). However, the caveat is that, in principle, the waveform morphology is unlikely to be fully characterized by a single or multiple metrics. In other words, metric-based approach usually results in loss of morphological information.

In another approach, the morphology of two signals can be compared directly by means of correlation analysis. High correlation between two signals indicates they have similar morphology, whereas low correlation indicates they have different morphology. The most commonly used correlation measure is the Pearson's Correlation Coefficient (PCC). However, it has two major limitations. First, the calculation of PCC requires floating point operation, which renders it not feasible for implementation in the low-power embedded systems, particularly the battery-powered implantable cardiac devices. Second, PCC does not account for the amplitude difference between signals and is sensitive to the impulsive noise.

In view of above, there is a need to provide the implantable cardiac devices a novel method to accurately, efficiently, and robustly perform IEGM morphology analysis, to facilitate sense event classification.

BRIEF SUMMARY OF THE INVENTION

It is an object of the invention to provide a device, for example an implantable cardiac device, such as a pacemaker, a defibrillator, a cardioverter or a biventricular pacing device, that can sense cardiac electrical signals and accurately classify the sensed events. The device comprises means for providing a template signal and a test signal originated from an electrogram. The template signal and the test signal comprising samples. The device comprises further means for transforming at least the test signal resulting in a representation of the test signal where the sample values of the signal take integers. The device comprises further means for determining a correlation between the template signal and the test signal, and means for classifying the sense events based on the correlation.

The electrogram may be an intracardiac electrogram (IEGM), an atrial electrogram (AEGM), a ventricular electrogram (VEGM), a surface electrocardiogram (ECG) or a subcutaneous electrogram.

In a preferred embodiment of the invention, the device comprising further means for constructing a normal atrial sense (AS) template waveform from the AEGM signal that corresponds to normal intrinsic atrial depolarization, for constructing a normal ventricular sense (VS) template waveform from the VEGM signal that corresponds to antegrade conducted ventricular depolarization, for constructing a retrograde AS template waveform from the AEGM signal that corresponds to retrograde atrial depolarization, or combinations thereof. The VS template waveforms can be further constructed for normal right ventricular (RV) sense event, and normal left ventricular (LV) sense event, respectively.

In a special embodiment, the inventive device provides means for constructing the normal atrial sense (AS) template waveform from the AEGM corresponding to the AS events detected outside the atrial refractory period (ARP), for constructing the normal ventricular sense (VS) template waveform from the VEGM corresponding to VS event that is outside the ventricular refractory period (VRP) and is associated with preceding AS event or atrial pace (AP) event, for constructing the retrograde AS template waveform from the AEGM corresponding to retrograde AS events, or combinations of such means. For confirming retrograde AS events, the device comprises in a further special embodiment means for determining the stability of intervals from the ventricular paces (VP) to the refractory atrial senses.

The invention provides a device which further comprises means for averaging a plurality of cycles of signals to obtain the template signal. Especially cycles of conducted ventricular IEGM signals may be used.

The invention provides a device which further comprises means for updating the template periodically or continuously after an initial template setup.

The invention provides a device which further comprises means for aligning the signals based on at least one predefined fiducial point.

In another preferred embodiment the inventive device comprises means for exposing the sense events, means for collecting multiple cycles of the IEGM signals containing the sense events, means for aligning the IEGM signals based on at least one predefined fiducial point; and means for creating the sense template waveform by averaging similarly aligned IEGM cycles.

A further object of the invention is providing a device which further comprises means for associating the template signal with at least two subspaces of the template signal space and means for transforming at least one of the template signal and the test signal with respect to the subspaces.

In an embodiment the means for associating the template signal with at least two subspaces comprises means for defining a first subspace comprising values which differ from the template signal values at the most by a predefined first value, and means for defining a second subspace comprising values which differ from the template signal values at the least by the predefined first value.

In another embodiment the means for associating the template signal with at least two subspaces comprises means for associating the template signal with three subspaces, and means for defining a first subspace comprising values which differ from the template signal values at the most by a predefined first value, means for defining a second subspace comprising values which differ from the template signal values at the least by the predefined first value and at the most by a predefined second value, and means for defining a third subspace comprising values which differ from the template signal values at the least by the predefined second value.

According to another aspect of the invention the device further comprising means for generating threshold vectors bounding the subspaces, where the threshold vectors are generated by increasing or decreasing the sample values of the template signal by a predefined fix value, or by a predefined ratio, or by their combinations.

According to yet another aspect of the invention the means for transforming comprises means for setting a sample value of the transformed signal to a first, second or third integer if the corresponding sample value of the signal belongs to the first, second or third subspace. In a special embodiment the first integer is set to 1, the second integer is set to 0 and the third integer is set to −1.

In a further embodiment of the invention the device comprises means for determining a correlation using at least the transformed test signal.

In yet a further embodiment of the invention the device comprises means for determining a correlation using only the transformed test signal.

In another embodiment the means for determining a correlation comprises means for determining an Adapted Signed Correlation Index (ASCI) as the sum of the sample values of the transformed test signal or by dividing the sum of the sample values of the transformed test signal by the number of samples.

It is a further object of the invention to provide a device which comprises means for detecting ectopic beat events by calculating the correlation between templates and test signals based on morphological analysis, especially based on ASCI-based morphological analysis. Preferably, such a device comprises means for determining correlation between a normal AS template and a test AEGM signal, and means for indicating, depending from the correlation value, a normal intrinsic AS event or an atrial extra-systole (AES) event. An alternative embodiment comprising means for determining correlation between a normal VS template and a test VEGM signal, and means for indicating, depending from the correlation value, a normal intrinsic VS template or a ventricular extra-systole (VES) event. Also combinations of the both embodiments are possible.

In a further preferred embodiment, the ASCI-based morphological analysis is combined with at least time interval analysis, and signal processing algorithms for ectopic beat detection in devices or systems (e.g., ECG monitors, ECG Holters, etc.) involving measurement and analysis of surface ECG signals. Yet another preferred device comprises means for activating the ectopic beat detection only when the time interval analysis could not definitely differentiate normal beat from ectopic beat. However, ectopic beat detection may also be conducted independent from a time interval analysis.

It is a further object of the invention to provide a device comprising means for differentiating retrograde atrial depolarization from normal intrinsic atrial depolarization by calculating the correlation between templates based on morphological analysis, especially based on ASCI-based morphological analysis. In a preferred embodiment, the device for differentiating retrograde atrial depolarization from normal intrinsic atrial depolarization comprises means for calculating for an AS event detected within the post-ventricular atrial refractory period (PVARP) a first correlation value by comparing the corresponding AEGM with a normal AS template, means for indicating, depending from the first correlation value, the event as a normal intrinsic AS or not, and then calculating a second correlation value by comparing the corresponding AEGM with a retrograde AS template, and means for indicating, depending from the second correlation value, the event as a retrograde AS or neither a normal intrinsic AS, nor a retrograde AS. In a preferred embodiment, the device is arranged in such a way that an event is ignored, if the event is indicated as neither a normal intrinsic AS, nor a retrograde AS.

Preferably, the device for differentiating retrograde atrial depolarization from normal intrinsic atrial depolarization is also combined with a time interval analysis.

It is a further object of the invention to provide a device comprising means for far field sensing classification by calculating the correlation between templates based on morphological analysis, especially based on ASCI-based morphological analysis. In a preferred embodiment, the device for far field sensing comprises means for calculating for an AS event detected within a far-field blanking (FFB) window a first correlation value by comparing the corresponding AEGM with a normal AS template, means for indicating, depending from the first correlation value, the event as a normal intrinsic AS or not, then further checking whether the AS event detected within the FFB is preceded by a VP or a VES event, means for calculating, depending from the result of the check, a second correlation value by comparing the corresponding AEGM with a retrograde AS template, and means for indicating, depending from the second correlation value, the event as a retrograde AS or neither a normal intrinsic AS, nor a retrograde AS. In a special embodiment, the device for far field sensing is arranged that an AS event in FFB is ignored, if the event is not preceded by a VP or a VES event, or if the event is indicated as neither a normal intrinsic AS, nor a retrograde AS.

In a further preferred embodiment the device for far field sensing comprises at least one of means for calculating a correlation value by comparing the corresponding RV IEGM with the normal RV sense template, if an RV event is detected within the FFB of a preceding LV event, and indicating, depending from the correlation value, the RV sense event as a normal intrinsic RV sense or as a VES, a far-field sense, or a noise sense, and similarly, calculating a correlation value by comparing the corresponding LV IEGM with the normal LV sense template, if an LV sense event is detected within the FFB of a preceding RV event, and indicating, depending from the correlation value, the LV sense event as a normal intrinsic LV sense or as a VES, a far-field sense, or a noise sense. Such a device may be arranged for ignoring the RV or the LV sense event if it is indicated as VES, far-field sense, or noise sense.

Preferably, the device for far field sensing is also combined with a time interval analysis.

It is further an objective of the invention to provide a method for classifying sense events in implantable devices using signals provided by an electrogram comprising the steps of:

providing a template signal and a test signal, the template signal and the test signal comprising samples;

transforming at least the test signal resulting in a representation of the test signal where the sample values of the signal take integers;

determining a correlation between the template signal and the test signal; and classifying the sense event based on the correlation.

According to an aspect of the invention the signals are provided by an intracardiac electrogram (IEGM), an atrial electrogram (AEGM), a ventricular electrogram (VEGM), a surface electrocardiogram (ECG) or a subcutaneous electrogram.

In a preferred embodiment of the invention, the method for classifying sense events in implantable devices comprising means for constructing and maintaining:

a normal atrial sense (AS) template waveform from the AEGM signal that corresponds to normal intrinsic atrial depolarization;

a normal ventricular sense (VS) template waveform from the VEGM signal that corresponds to antegrade conducted ventricular depolarization;

a retrograde AS template waveform from the AEGM signal that corresponds to retrograde atrial depolarization;

a normal right ventricular (RV) sense template that corresponds to normal intrinsic RV depolarization; and a normal left ventricular (LV) sense template that corresponds to normal intrinsic LV depolarization.

Normal RV sense templates and normal LV sense templates are respectively constructed and maintained especially in a biventricular pacing device.

Especially, construction of a template waveform may be performed, where the normal atrial sense (AS) template waveform is constructed from the AEGM corresponding to the AS events detected outside the atrial refractory period (ARP);

the normal ventricular sense (VS) template waveform is constructed from the VEGM corresponding to VS event that is outside the ventricular refractory period (VRP) and is associated with preceding AS event or atrial pace (AP) event; and the retrograde AS template waveform is constructed from the AEGM corresponding to retrograde AS events. The retrograde AS event may be confirmed by relatively stable intervals from the ventricular paces (VP) to the refractory atrial senses.

In a further embodiment of the inventive method it is proposed, that construction of the sense template waveform comprises the following steps:
  exposing the sense event;
  collecting multiple cycles of the IEGM signals containing the sense event;
  aligning the IEGM signals based on at least one predefined fiducial point; and
  creating the sense template waveform by averaging similarly aligned IEGM cycles.

In an embodiment of the invention the template signal is obtained by averaging a plurality of cycles of signals.

In an embodiment of the invention after an initial template setup the template is updated periodically or continuously.

In another embodiment of the invention the signals are aligned based on at least one predefined fiducial point.

According to another aspect of the invention the method for classifying sense events in implantable devices comprises the further steps of:
  associating the template signal with at least two subspaces of the template signal space and
  transforming at least one of the template signal and the test signal with respect to the subspaces.

In an embodiment of the invention the at least two subspaces are defined by
  a first subspace comprising values which differ from the template signal values at the most by a predefined first value, and
  a second subspace comprising values which differ from the template signal values at the least by the predefined first value.

In another embodiment of the invention the template signal is associated with three subspaces and the three subspaces are defined by
  a first subspace comprising values which differ from the template signal values at the most by a predefined first value,
  a second subspace comprising values which differ from the template signal values at the least by the predefined first value and at the most by a predefined second value, and
  a third subspace comprising values which differ from the template signal values at the least by the predefined second value.

According to an aspect of the invention the subspaces are bounded by threshold vectors.

In an embodiment of the invention the threshold vectors are obtained by increasing or decreasing the sample values of the template signal by a predefined fix value, or by a predefined ratio, or by their combinations.

In an embodiment of the invention transforming the signals comprises assigning a first, second or third integer to a sample of the transformed signal if the corresponding sample of the signal belongs to the first, second or third subspace. The first integer may be set to 1, the second integer may be set to 0 and the third integer may be set to −1.

According to an aspect of the invention determination of the correlation is performed using at least the transformed test signals.

According to another aspect of the invention determination of the correlation is performed using only the transformed test signal.

In an embodiment of the invention for determining a correlation, an ASCI is determined as the sum of the sample values of the transformed test signal or by dividing the sum of the sample values of the transformed test signal by the number of samples.

An aspect of the present invention is to provide a method for detecting ectopic beat events by calculating the correlation between templates based on morphological analysis, especially based on ASCI-based morphological analysis.

According to a preferred embodiment the method for detecting ectopic beat events comprises the steps of:
  determining correlation between a normal AS template and a test AEGM signal, and
  depending from the correlation value indicating a normal intrinsic AS event or an atrial extra-systole (AES) event.

In an alternative embodiment the method for detecting ectopic beat events comprises the steps of:
  determining correlation between a normal VS template and a test VEGM signal, and
  depending from the correlation value indicating a normal intrinsic VS template or an ventricular extra-systole (VES) event.

A further embodiment proposes that the ASCI-based morphological analysis is combined with at least time interval analysis, and signal processing algorithms for ectopic beat detection in devices or systems involving measurement and analysis of surface ECG signals.

It may be also advantageous, that the ectopic beat detection is only activated when the time interval analysis could not definitely differentiate normal beat from ectopic beat.

It is a further object of the present invention to provide a method for differentiating retrograde atrial depolarization from normal intrinsic atrial depolarization by calculating the correlation between templates based on morphological analysis, especially based on ASCI-based morphological analysis.

In a preferred embodiment of the method for differentiating retrograde atrial depolarization from normal intrinsic atrial depolarization for an AS event detected within the post-ventricular atrial refractory period (PVARP) a first correlation value is calculated by comparing the corresponding AEGM with a normal AS template, depending from the first correlation value the event is indicated as a normal intrinsic AS or not, then a second correlation value is calculated by comparing the corresponding AEGM with a retrograde AS template; and depending from the second correlation value the event is indicated as a retrograde AS or neither a normal intrinsic AS, nor a retrograde AS. Preferably, an event is ignored if the event is indicated as neither a normal intrinsic AS, nor a retrograde AS.

It is a further object of the invention to provide a method for performing far field sensing classification by calculating the correlation between templates based on morphological analysis, especially based on ASCI-based morphological analysis.

The far field sensing classification method comprises in a preferred embodiment at least the following steps:
  calculating for an AS event detected within a far-field blanking (FFB) window a first correlation value by comparing the corresponding AEGM with a normal AS template;
  depending from the first correlation value indicating the event as a normal intrinsic AS or not, and further checking whether the AS event detected within the FFB is preceded by a VP or a VES event;
  depending from the result of the check calculating a second correlation value by comparing the corresponding AEGM with a retrograde AS template; and
  depending from the second correlation value indicating the event as a retrograde AS or neither a normal intrinsic AS, nor a retrograde AS.

Within the method far field sensing event may be ignored if the AS event in FFB is not preceded by a VP or a VES event, and/or an event may be ignored if the event is indicated as neither a normal intrinsic AS, nor a retrograde AS.

According to an embodiment of the method for far field sensing, a correlation value is calculated for an RV sense event detected within the FFB of a preceding LV event by comparing the corresponding RV IEGM with the normal RV sense template and, depending from the correlation value, the RV sense event is indicated as a normal intrinsic RV sense or a VES, a far-field sense, or a noise sense. Similarly, a correlation value is calculated for an LV sense event detected within the FFB of a preceding RV event by comparing the corresponding LV IEGM with the normal LV sense template and, depending from the correlation value, the LV sense event is indicated as a normal intrinsic LV sense or a VES, a far-field sense, or a noise sense. The RV sense event or the LV sense event may be ignored if it is indicated as VES, far-field sense, or noise sense.

In a preferred embodiment, the ASCI-based morphology analysis is used in conjunction with the time interval analysis for detecting atrial and/or ventricular ectopic beat events, for differentiating retrograde atrial depolarization from normal intrinsic atrial depolarization, and for performing far field sensing classification.

It is further an objective of the invention to provide a computer-readable storage medium storing program code for causing a data processing device to perform a method for classifying sense events in implantable devices using signals provided by an electrogram, the method comprising the steps of:
providing a template signal and a test signal, the template signal and the test signal comprising samples;
transforming at least the test signal resulting in a representation of the test signal where the sample values of the signal take integers;
determining a correlation between the template signal and the test signal; and
classifying the sense event based on the correlation.

According to this invention, a novel index called Adaptive Signed Correlation Index (ASCI) is used to quantify the morphology similarity between two IEGM waveforms. The calculation of ASCI is computationally efficient because no floating-point operation is necessary. Furthermore, calculation of ASCI is robust against measurement noise and minor alignment error of the signals.

In a typical embodiment, template signals are created and maintained to represent the normal atrial depolarization and normal ventricular depolarization, respectively. Preferably, the template waveforms are created by averaging multiple cycles of IEGM signals (all aligned with predefined fiducial point) representing normal intrinsic depolarization. The template waveforms are also preferably updated periodically or dynamically to reflect the gradual change of the IEGM morphology.

Upon a sensed atrial event or ventricular event, the corresponding IEGM waveform is compared to the respective template signal, and their similarity is quantified by the ASCI. High ASCI value that is greater than a predefined threshold indicates normal intrinsic cardiac activity, whereas low ASCI value that is lower than the predefined threshold indicates non-intrinsic cardiac activity or abnormal cardiac activity. Combined with time interval analysis, the ASCI-based morphology analysis improves accuracy of the event classification, thus enhancing the sensing function of the device.

The details of the invention can be understood from the following drawings and the corresponding text descriptions.

DETAILED DESCRIPTION OF THE INVENTION

Construction of Template Waveform

According to this invention, a normal atrial sense (AS) template waveform is constructed from the atrial electrogram (AEGM) signal that corresponds to normal intrinsic atrial depolarization. For implantable cardiac devices, the normal atrial template waveform can be constructed from the AEGM corresponding to the AS events detected outside the atrial refractory period (ARP). As known in the art, the normal AS events can be exposed by programming the device atrial pacing rate below the sinus rate of the heart.

Also according to this invention, a normal ventricular sense (VS) template waveform is constructed from the ventricular electrogram (VEGM) signal that corresponds to antegrade conducted ventricular depolarization. For implantable cardiac devices, the normal VS template can be constructed from the VEGM corresponding to VS event that is outside the ventricular refractory period (VRP) and is associated with preceding AS event or atrial pace (AP) event. As known in the art, the normal VS events can be exposed by programming device atrio-ventricular (AV) delay longer than the intrinsic AV conduction time.

Further according to this invention, a retrograde AS template waveform is constructed from the AEGM signal that corresponds to retrograde atrial depolarization. For implantable cardiac devices, the retrograde AS template can be constructed from the AEGM corresponding to retrograde AS events. As known in the art, the retrograde AS events can be exposed by programming device in VDI mode, programming ventricular pacing rate higher than the intrinsic heart rate, and programming a long post-ventricular atrial refractory period (PVARP). The retrograde AS events can be confirmed by relatively stable interval from the ventricular paces (VP) to the refractory atrial senses.

Figure 1:
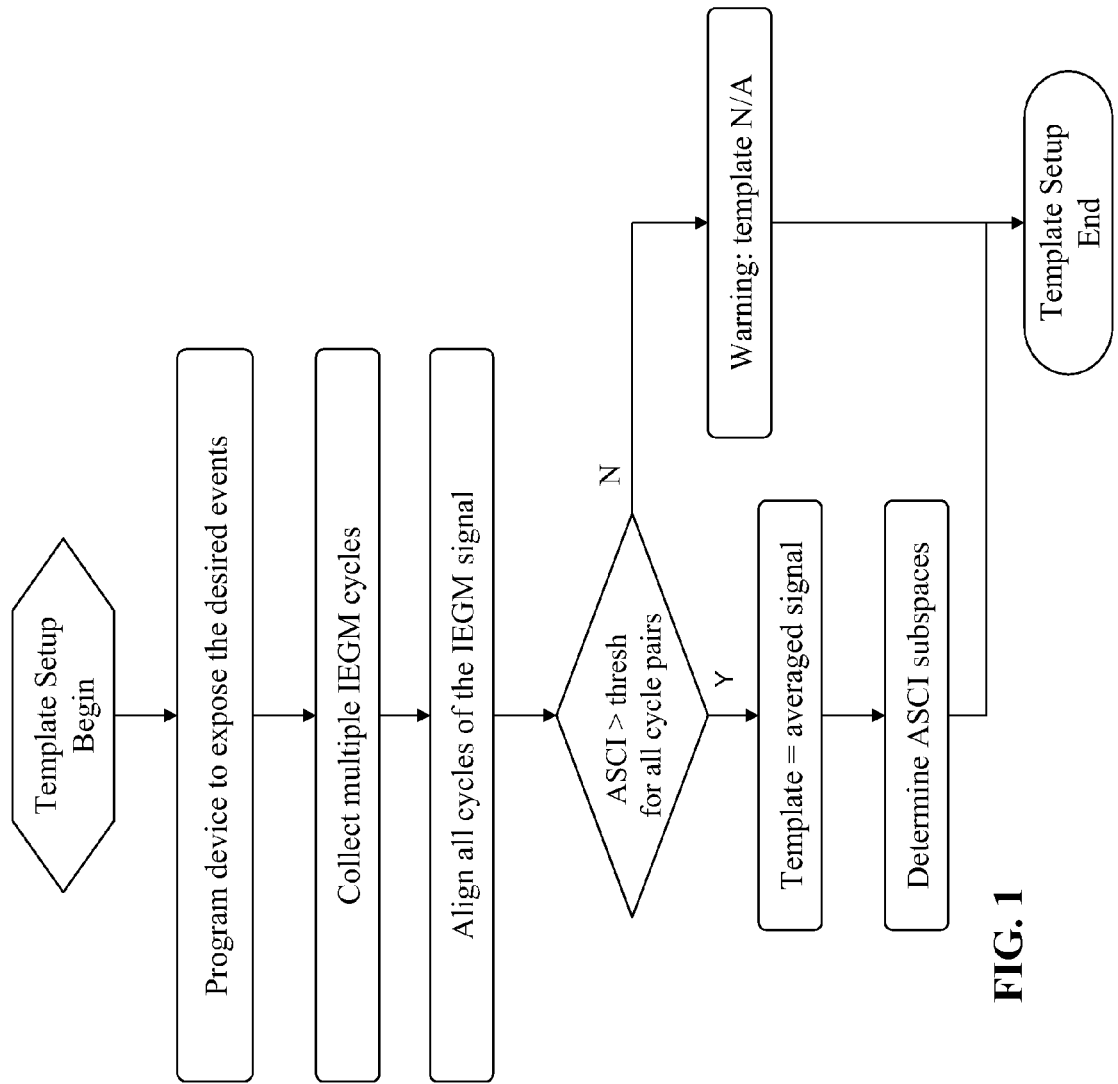
FIG. 1 is a high-level flowchart diagram that illustrates the steps involved in automatic setup of the IEGM template in an implantable cardiac device.

FIG. 1 shows a high-level flowchart diagram that illustrates the steps involved in automatic setup of the IEGM templates in an implantable cardiac device. The IEGM templates can be normal AS template, normal VS template, or retrograde AS template. Preferably, the automatic template setup is performed during initial device implant, or during regular device follow-up, when the physician can verify the template signal is constructed from valid IEGM signals.

As described above, to construct the desired IEGM templates (normal AS template, normal VS template, retrograde AS template), the device is programmed accordingly in order to expose the desired sense events (normal AS events, normal VS events, retrograde AS events). Then the device collects multiple cycles of the IEGM signals containing the desired sense events (normal AS, normal VS, retrograde AS). The IEGM signals are then aligned based on predefined fiducial point, for example, the positive or negative peak, the maximum slope, the threshold crossing point, etc., as known in the art. For each cycle, the IEGM segment in a fixed window relative to the fiducial point is selected for creating the template signal. In a typical embodiment, the fiducial point is chosen as the dominant peak (positive or negative) of the IEGM signal, and the IEGM window spans from 50 ms before the fiducial point to 100 ms after the fiducial point.

Still refer to FIG. 1. According to this invention, for each pair of the aligned and windowed IEGM signals, their morphological similarity is quantified by an Adaptive Signed Correlation Index (ASCI), which will be described in details in the following sections. If for any given cycle pair, the calculated ASCI is lower than a predefined threshold value, then the collected IEGM signals are considered not stable. A warning is generated by the device indicating the template signal is not available at the moment, and the template setup may be retried at a later time. On the other hand, if for all cycle pairs, the calculated ASCI is greater than the predefined threshold value (e.g., 0.8), then all collected IEGM cycles are considered similar, and the desired IEGM template is created by averaging all these aligned IEGM cycles.

As discussed in more details later, the ASCI is calculated based on the definition of three subspaces that are dependent on the template signal. Thus upon creation of the IEGM template, the device further determines the three subspaces as discussed thereinafter. Note that during the initial template setup phase when template waveform has not been available yet, to calculate the ASCI between a pair of IEGM cycles, any one of the two IEGM signals can be initialized as the tentative template signal. Based on this tentative template signal, the three subspaces can be defined, and the similarity between these two signals can be quantified by ASCI. As discussed above, only if all pairs of the collected IEGM cycles result in higher than predefined ASCI threshold, then these cycles are considered to have similar morphology, and the true template waveform can be created.

Figure 2:
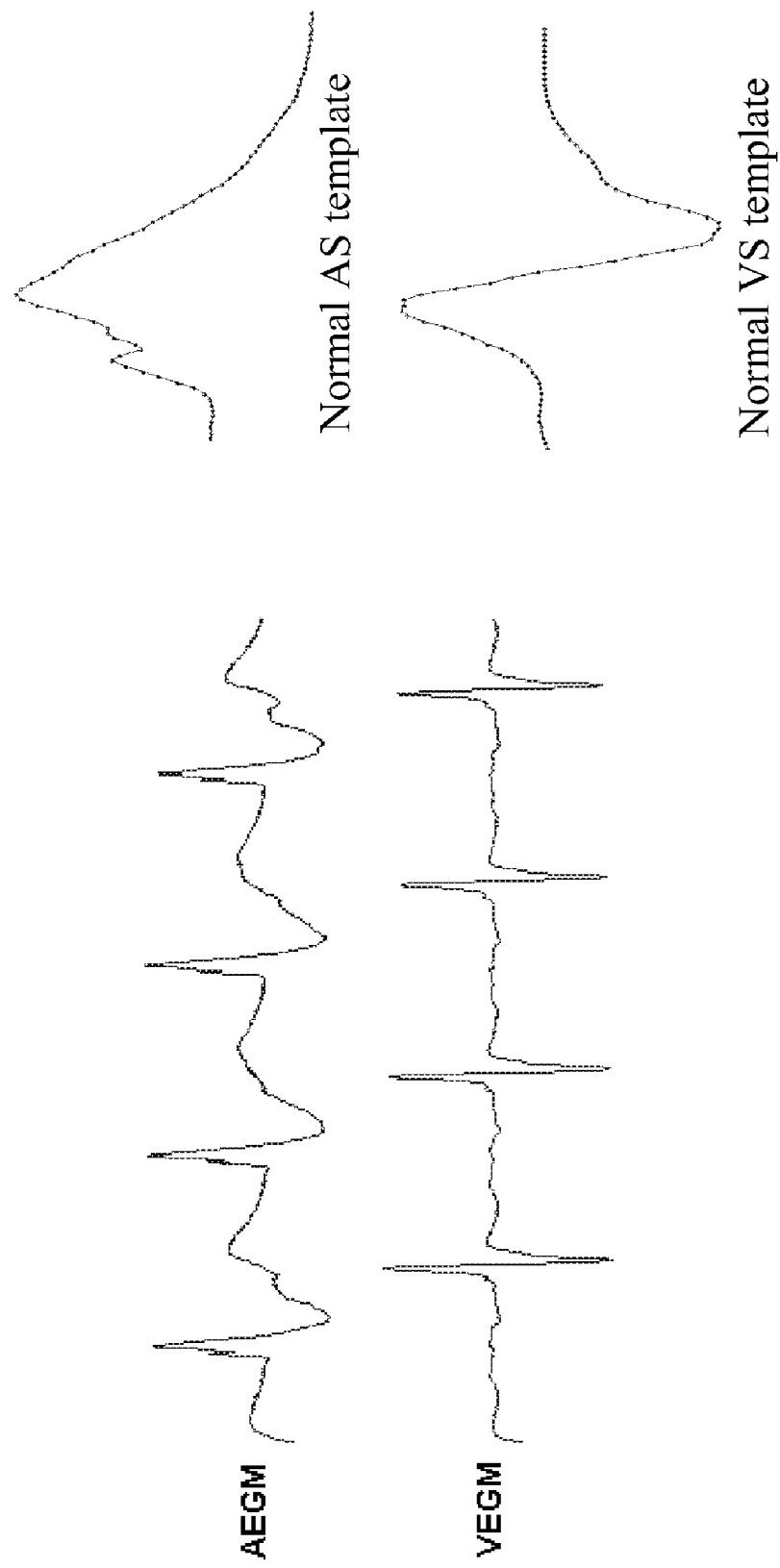
FIG. 2 shows an example of template setup for normal AS events and normal VS events.

FIG. 2 shows a particular example of setting up normal AS template and normal VS template. In this example, the AEGM and the VEGM are shown in the left for four cardiac cycles in sinus rhythm. Each intrinsic atrial depolarization is followed by a conducted ventricular depolarization. Both AEGM and VEGM morphology are consistent among the four cycles. For both AEGM and VEGM, the positive peak is chosen as the fiducial point, and the window size is set from 50 ms before the positive peak to 100 ms after the positive peak. Then the four cycles of AEGM are averaged to construct the normal AS template and the four cycles of VEGM are averaged to construct the normal VS template as shown in the right.

Update of Template Waveform

According to this invention, after the initial template setup, the normal AS template, the normal VS template, and the retrograde AS template are preferably updated periodically or continuously to reflect the dynamic change of the corresponding IEGM morphology. This template running update feature is important because the normal AS, normal VS, and retrograde AS waveforms may gradually change over time due to different factors such as heart rate variation, circadian pattern, changes of medication, changes of electrode-tissue interface, etc.

Figure 3:
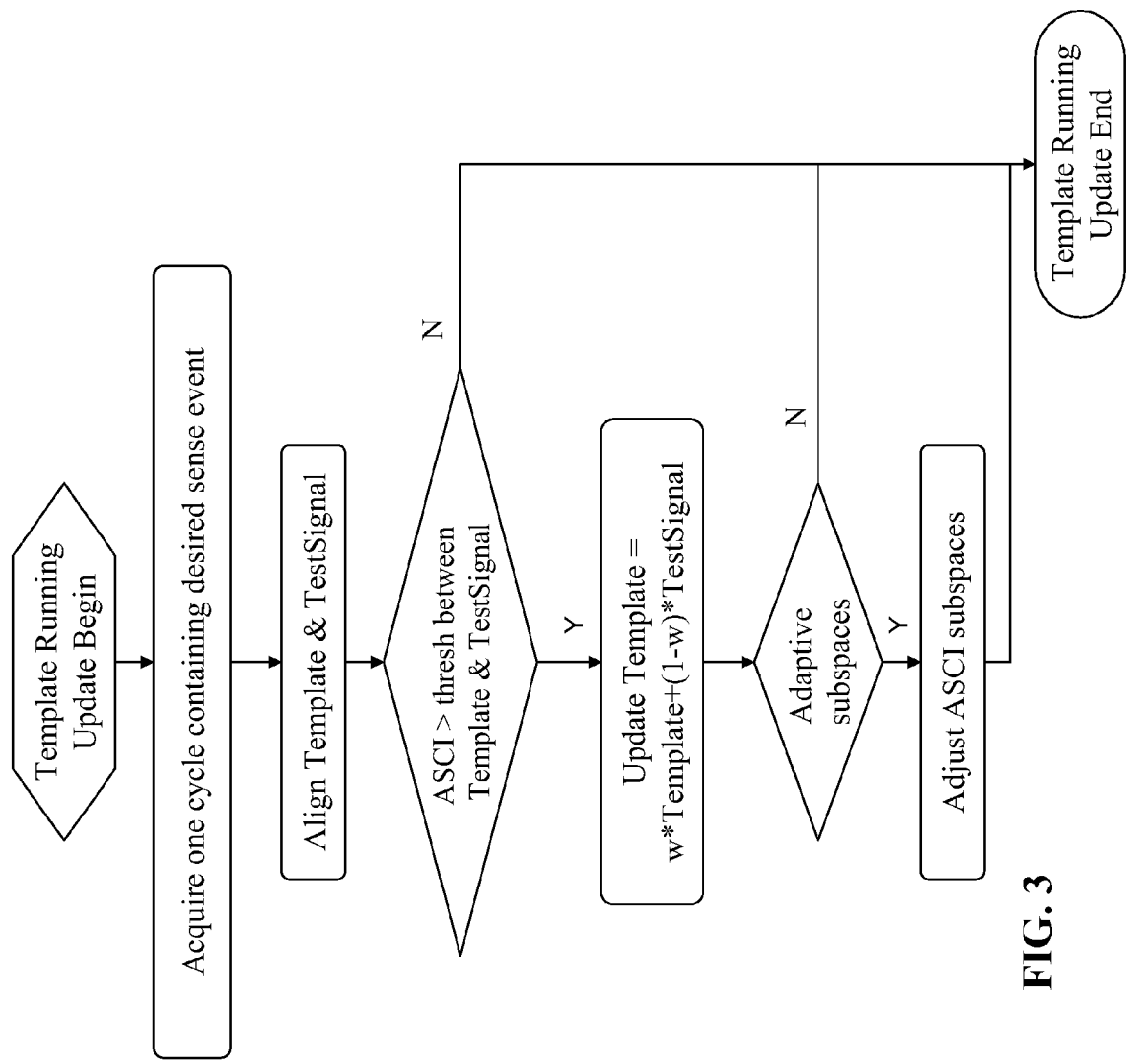
FIG. 3 shows a high-level flowchart that illustrates the steps involved in running update of the IEGM template in an implantable cardiac device.

FIG. 3 shows a high-level flowchart that illustrates the steps involved in running update of the IEGM templates (normal AS template, normal VS template, retrograde AS template). Preferably, the template running update is activated only when a detected sense event is considered likely to be the desired event type. For example, a detected AS event outside the ARP is likely a normal AS event, a detected VS event outside the VRS and preceded by an AS or AP event is likely a normal VS event, and a detected AS event following a VP event and inside the PVARP is likely a retrograde AS event.

Upon detection of the likely desired sense event (normal AS, normal VS, or retrograde AS), the device acquires one cycle of the corresponding AEGM (for normal AS or retrograde AS) or VEGM (for normal VS) as the test signal, which is aligned with the corresponding template signal (normal AS template, normal VS template, retrograde AS template) based on predefined fiducial point as discussed above.

Then the device calculates the ASCI between the acquired test signal and the corresponding template signal. If the ASCI is lower than a predefined threshold (e.g., 0.8), then the test signal is considered different than the template signal, and no template update is performed for this test cycle. On the other hand, if the calculated ASCI is greater than the predefined threshold (e.g., 0.8), then the test signal is considered similar to the template signal, and the template signal is updated by taking the weighted average of the original template signal and the newly acquired test signal. In an exemplary embodiment, the new template is the sum of the old template signal scaled by $255/256$, and the newly acquired test signal scaled by $1/256$. By this means, it ensures the stability of the template waveform by retaining $255/256$ of the old template signal, whereas it incorporates $1/256$ of the test signal to factor in any gradual change of the IEGM morphology of the corresponding event type.

As discussed in more details later, the ASCI is calculated based on the definition of three subspaces which are dependent on the template signal. Thus the device can further adjust the three subspaces based on newly updated template signal, if the adaptive subspace feature is enabled.

Signal Alignment

One prerequisite for any morphology-based event classification algorithms is that the test signal must be properly aligned with the template signal. Morphological analysis based on misaligned signals may yield misleading results. As discussed above, the common practice for signal alignment is based on a predefined fiducial point, such as the positive peak, the negative peak, etc. However, in some cases, the signal alignment based on a single fiducial point is not reliable.

Figure 4:
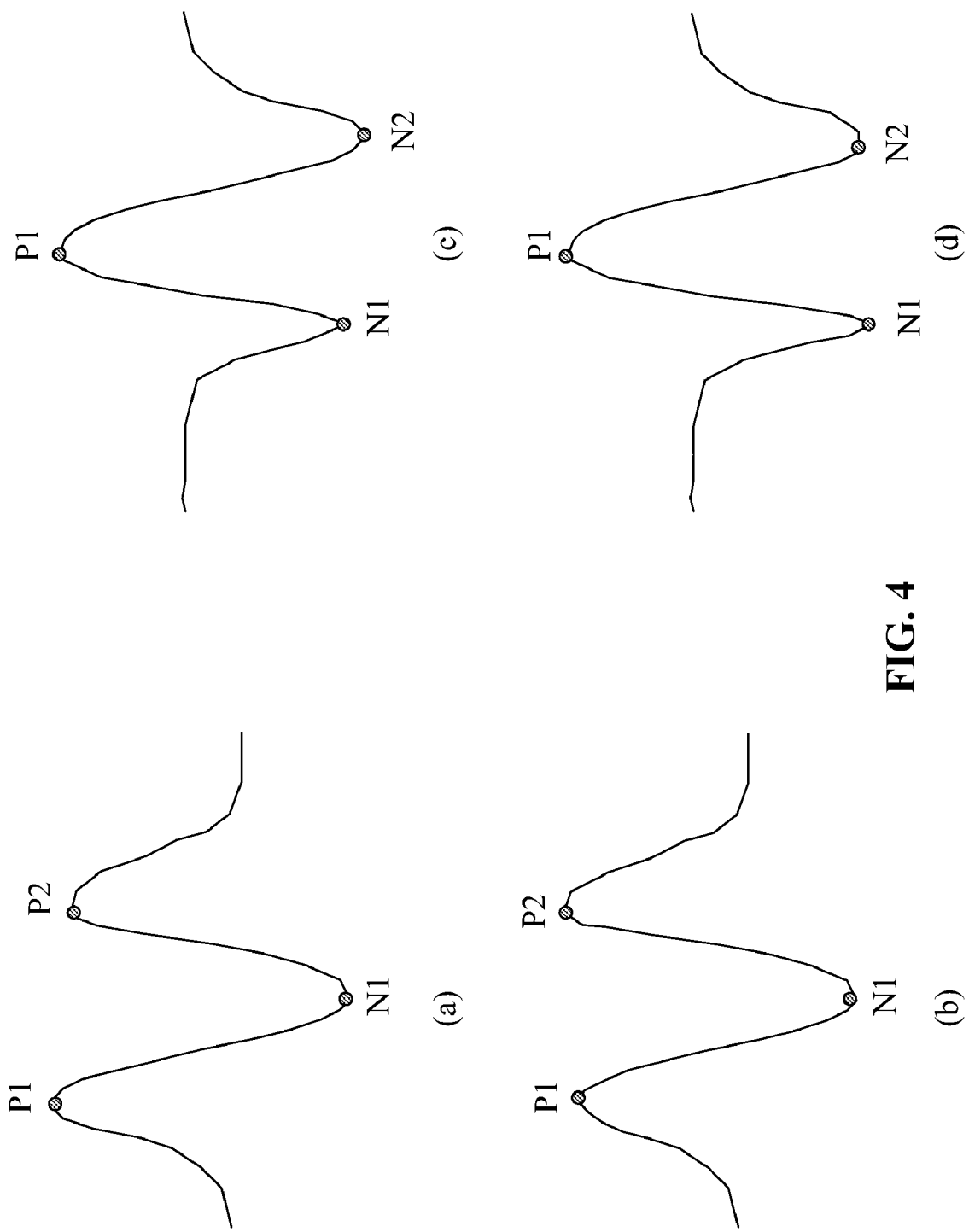
FIG. 4 illustrates the concept of signal alignment using multiple fiducial points.

FIG. 4 shows some examples. Panels (a) and (b) show two signal complexes that have similar morphology. Both signal complexes can be characterized by two positive peaks (P1, P2) that have similar amplitude and one negative peak (N1). If the dominant positive peak is chosen as the fiducial point, then the fiducial point will be P1 for the signal complex shown in panel (a) but P2 for the signal complex shown in panel (b). Similarly, panels (c) and (d) show another pair of signal complexes that have similar morphology. Both signal complexes can be characterized by two negative peaks (N1, N2) that have similar amplitude and one positive peak (P1). If the dominant negative peak is chosen as the fiducial point, then the fiducial point will be N2 for the signal complex shown in panel (c) but N1 for the signal complex shown in panel (d).

According to this invention, multiple fiducial points are defined for signal alignment in adjunction with ASCI-based morphological analysis. Specifically, for a given template signal representing the desired event type (normal AS, normal VS, retrograde AS), multiple fiducial points (if available) are defined in a sequential order, that is, $1^{st}$ fiducial point, $2^{nd}$ fiducial point, $3^{rd}$ fiducial point, etc. Similar fiducial points (if available) are also identified for a test IEGM signal. For example, for the signals shown in panels (a) and (b) of FIG. 4, the fiducial points can be defined in the following order: dominant positive peak (1$^{st}$ fiducial point; P1 in (a) and P2 in (b)), dominant negative peak (2$^{nd}$ fiducial point; N1 in both (a) and (b)), secondary positive peak (3$^{rd}$ fiducial point; P2 in (a) and P1 in (b)). Similarly, for the signals shown in panels (c) and (d) of FIG. 4, the fiducial points can be defined in the following order: dominant positive peak (1$^{st}$ fiducial point; P1 in both (c) and (d)), dominant negative peak (2$^{nd}$ fiducial point; N2 in (c) and N1 in (d)), secondary negative peak (3$^{rd}$ fiducial point; N1 in (c) and N2 in (d)).

To compare the morphology of a test signal and the corresponding template signal, the two signals are first aligned with the 1$^{st}$ fiducial point, and their ASCI value is calculated. If the resulting ASCI value is higher than a predefined threshold (e.g., 0.8), then it indicates the two signals have similar morphology. The signal alignment is considered valid, and no further calculation is needed. On the other hand, if the resulting ASCI value is lower than the predefined threshold (e.g., 0.8), then it indicates the two signals have different morphology. Then the signals are re-aligned with the 2$^{nd}$ fiducial point (if available for both signals), and their ASCI value is re-calculated. If the re-calculated ASCI value is higher than the predefined threshold (e.g., 0.8), then it indicates misalignment for the 1$^{st}$ fiducial point, but the alignment based on the 2$^{nd}$ fiducial point is valid. The signals are considered to have similar morphology and no further calculation is needed. Similar test can be performed for the 3$^{rd}$ fiducial point (if available for both signals) if the ASCI value obtained for the 2$^{nd}$ fiducial point is still lower than the predefined threshold (e.g., 0.8). No further test is needed if a fiducial point is only available for one signal but not the other signal. If all ASCI values are below the predefined threshold (e.g., 0.8), no matter which fiducial point is chosen, then it is determined that the test signal and the template signal have different morphology.

According to the experience of the present inventors, using two fiducial points (e.g., dominant positive peak and dominant negative peak) for signal alignment can effectively solve most of the signal misalignment problems caused by using a single fiducial point.

Definition of Adaptive Subspaces

Figure 5:
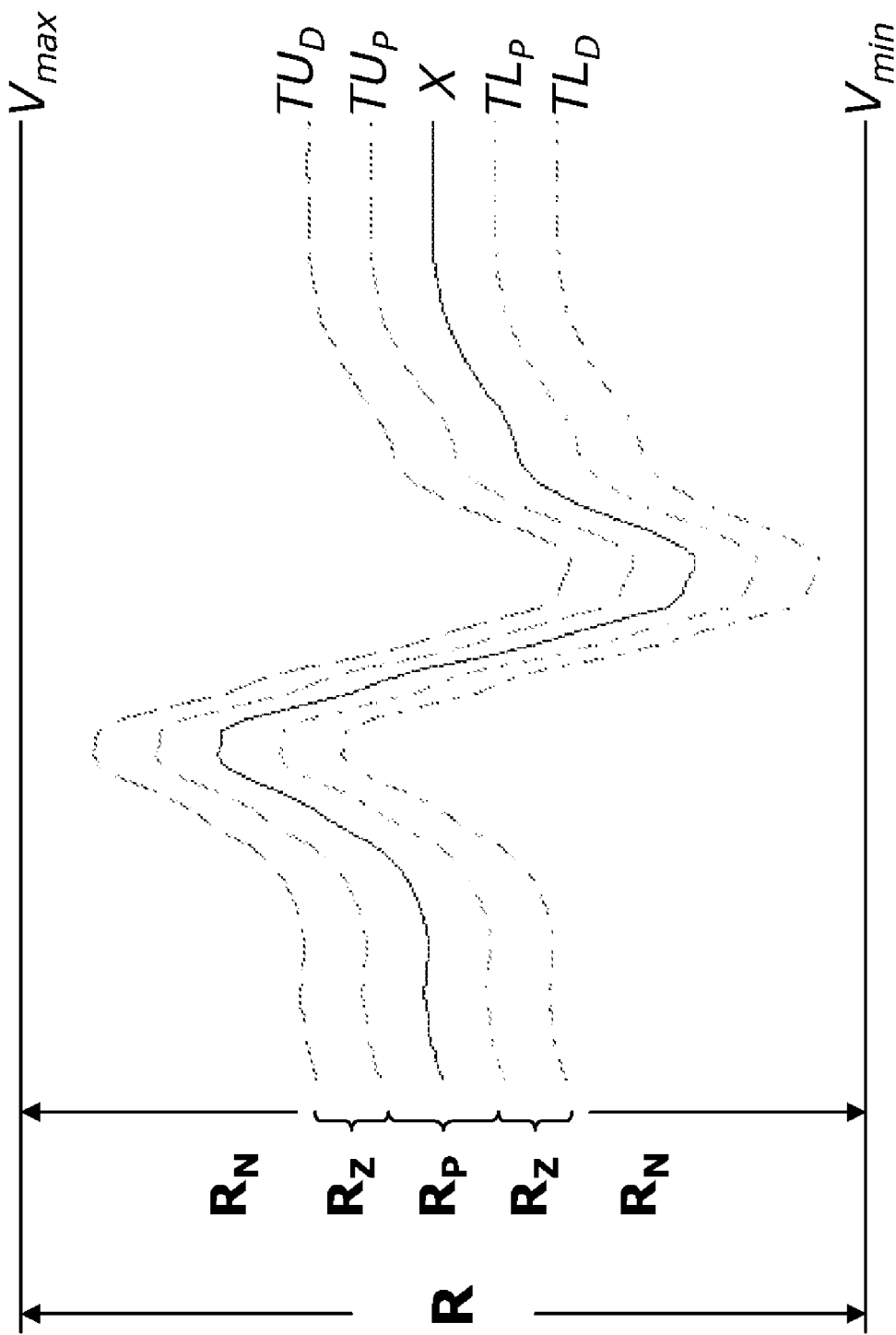
FIG. 5 illustrates the concept of three subspaces defined by four threshold vectors that are adaptive to the template signal.

Refer to FIG. 5. Let R denote the IEGM signal space that spans from $V_{min}$ to $V_{max}$, where $V_{min}$ is the minimum amplitude and $V_{max}$ is the maximum amplitude that could be measured by the sensing channel of the device. Divide R into three subspaces $R_P$, $R_Z$, and $R_N$ such that $R = R_P \cup R_Z \cup R_N$ and $R_P \cap R_Z = R_P \cap R_N = R_Z \cap R_N = \emptyset$, where $\cup$ is the union operator, $\cap$ is the intersection operator, and $\emptyset$ represents the null space. That is, the three subspaces are non-overlapping yet all together they span the whole signal space. For convenient purpose, in the following descriptions, we term $R_P$ as the positive subspace, $R_Z$ as the zero subspace, and $R_N$ as the negative subspace.

Still refer to FIG. 5. According to this invention, all three subspaces ($R_P$, $R_Z$, $R_N$) are adaptive to the template signal representing IEGM morphology of the desired event type (normal AS, normal VS, or retrograde AS). In a preferred embodiment, four threshold vectors $TL_D$, $TL_P$, $TU_P$, $TU_D$ are defined from the template signal X. Denote X=[x(1), x(2), ..., x(L)], where L is the number of samples in signal X. Further denote $TL_P$=[tlp(1), tlp(2), ..., tlp(L)] as the proximal lower threshold vector, $TL_D$=[tld(1), tld(2), ..., tld(L)] as the distal lower threshold vector, $TU_P$=[tup(1), tup(2), ..., tup(L)] as the proximal upper threshold vector, and $TU_D$=[tud(1), tud(2), ..., tud(L)] as the distal upper threshold vector. These threshold vectors are defined such that $TL_D \leq TL_P \leq X \leq TU_P \leq TU_D$, or specifically, tld(i)$\leq$tlp(i)$\leq$x(i)$\leq$tup(i)$\leq$tud(i), for $1 \leq i \leq L$. The positive subspace $R_P$ is defined as the region bounded by $TL_P$ and $TU_P$, the negative subspace $R_N$ is defined as the region above $TU_D$ or below $TL_D$, and the zero subspace $R_Z$ is defined as the region bounded between $TU_P$ and $TU_D$, and that between $TL_D$ and $TL_P$. Obviously, a sample in $R_P$ is proximal to the template, a sample in $R_N$ is distal to the template, and a sample in $R_Z$ is at intermediate distance to the template.

According to an exemplary embodiment of the present invention, the four threshold vectors are defined from the template signal according to the following equations:

$$TU_P = X + \alpha \cdot \max(abs(X))$$

$$TL_P = X - \alpha \cdot \max(abs(X))$$

$$TU_D = X + \beta \cdot \max(abs(X))$$

$$TL_D = X - \beta \cdot \max(abs(X))$$

Here, max(abs(X)) is the peak absolute amplitude of the template signal, $\alpha$ and $\beta$ are programmable scaling coefficients that satisfy $0 < \alpha < \beta$. In a typical example, $\alpha=0.25$ and $\beta=0.5$, and the resulting threshold vectors are symmetric around the template signal.

Obviously, there are numerous other means to define the four threshold vectors so that they are adaptive to the template signal X, for example, either based on sample-by-sample amplitude of X, or based on specific features of X, such as its maximum, minimum, max absolute, mean, median, etc., or their combinations. Also, the upper threshold vectors and the lower threshold vectors can be symmetric or asymmetric around the template signal.

As illustrated in FIG. 1, after automatic setup of the IEGM template, the three subspaces can be defined from four threshold vectors that are adaptive to the template signal by means of the method described above. Similarly, during the template running update as illustrated in FIG. 3, after the template signal is updated by taking the weighted average of the old template signal and the new test signal, the three subspaces can be adjusted by redefining the threshold vectors based on the new template.

Signal Trichotomization

To calculate the ASCI between two IEGM signals, both signals are first trichotomized based on three subspaces that are adaptive to the defined template signal.

Denote S as the three-value set $\{-1, 0, 1\}$. Assume X=[x(1), x(2), ..., x(L)] is an IEGM signal, that is, x(i) $\in$ R for i=1, 2, ..., L, where L is the number of samples in signal X. Trichotomization of signal X is an operation that maps the signal from R space to S space. Specifically, denote TX=[tx(1), tx(2), ..., tx(L)] as the trichotomized signal of X, where tx(i) $\in$ S for i=1, 2, ..., L. Then the trichotomization is formulated as:

$$tx(i) = \begin{cases} 1 & \text{if } x(i) \in R_P \\ 0 & \text{if } x(i) \in R_Z \\ -1 & \text{if } x(i) \in R_N \end{cases}$$

In other words, signal X is trichotomized to TX by converting all its data samples to values selected from $\{-1, 0, 1\}$, based on which subspace each data sample belongs to.

In a typical embodiment, signal X is the template signal of the desired event type (normal AS, normal VS, or retrograde AS), and ASCI(X,Y) measures the morphological similarity between a test IEGM signal Y and the template signal X. For the template signal X, all elements of its trichotomized signal TX are 1s because all samples of X are within the positive subspace $R_P$. For another signal Y, its trichotomized signal TY will have more 1s if more samples of Y are close to the corresponding samples of X, i.e., Y is similar to X. As Y gradually deviates from X, its trichotomized signal TY has less 1s, more 0s, and eventually more −1s.

Calculation of ASCI

Assume X=[x(1), x(2), . . . , x(L)] and Y=[y(1), y(2), . . . , y(L)] are two signals in R, and each has L samples. Given defined subspaces $R_P$, $R_Z$, and $R_N$ (which are adaptive to the template signal), X is trichotomized to TX=[tx(1), tx(2), . . . , tx(L)], and Y is trichotomized to TY=[ty(1), ty(2), . . . , ty(L)]. The ASCI between X and Y, or ASCI(X,Y), which measures the similarity between X and Y, is defined by the following formula:

$$ASCI(X, Y) = \frac{TX \circ TY}{\sqrt{TX \circ TX} \cdot \sqrt{TY \circ TY}}$$

Here, the symbol ∘ denotes the signed correlation (SC) of two trichotomized vectors, and is defined by the following formula:

$$TX \circ TY = \sum_{i=1}^{L} tx(i) \otimes ty(i)$$

Here, the symbol ⊗ denotes the signed product (SP) between two trichotomized scalars, and is defined by the following formula:

$$tx(i) \otimes ty(i) = \begin{cases} 1 & \text{if } tx(i) = ty(i) \\ -1 & \text{if } tx(i) \cdot ty(i) = -1 \\ 0 & \text{otherwise} \end{cases}$$

Accordingly, if tx(i)=ty(i), their SP is 1. In this case, the sample pair x(i) and y(i) are considered concordant, meaning that they are in the same subspace. Specifically, both are in the positive subspace if tx(i)=ty(i)=1; or both are in the negative subspace if tx(i)=ty(i)=−1; or both are in the zero subspace if tx(i)=ty(i)=0.

On the other hand, if tx(i)·ty(i)=−1, their SP is −1. In this case, the sample pair x(i) and y(i) are considered discordant. Specifically, it occurs when tx(i)=1 and ty(i)=−1, or tx(i)=−1 and ty(i)=1. In both cases, one sample is in the positive subspace whereas the other sample is in the negative subspace.

Otherwise, the case must be either tx(i)=0 and ty(i)≠0, or tx(i)≠0 and ty(i)=0, and their SP is 0. In this case, the sample pair x(i) and y(i) are considered neither concordant, nor discordant. Specifically, one sample is within the zero subspace, and the other sample is either in the positive subspace or in the negative subspace.

According to the above definition, the SC of two trichotomized vectors (TX∘TY) is the sum of the SP of all sample pairs tx(i)⊗ty(i), for i=1 . . . L. Therefore, the SC of two trichotomized signals will be increased by each pair of concordant samples (+1), decreased by each pair of discordant samples (−1), and not affected otherwise (neither concordant nor discordant sample pair).

For two identical signals, all corresponding sample pairs are concordant. Therefore, for above defined TX and TY, it is evident that TX∘TX=L and TY∘TY=L. Consequently, the formula for calculating ASCI(X,Y) defined above can be simplified to:

$$ASCI(X, Y) = \frac{TX \circ TY}{L}$$

As discussed above, in a typical embodiment, signal X is the template signal of the desired sense event (normal AS, normal VS, or retrograde AS), and all elements of its trichotomized signal TX are 1s because all samples of X are within the positive subspace. Thus, the formula for calculating ASCI(X, Y) defined above can be further simplified to:

$$ASCI(X, Y) = \frac{\sum_{i=1}^{L} ty(i)}{L}$$

In other words, the ASCI(X,Y) can be simply calculated as the cumulative sum of all trichotomized samples of test signal Y normalized by the number of samples.

Properties of ASCI

The definition of ASCI is compatible to the conventional definition of Pearson's correlation coefficient (PCC) Similar to PCC, ASCI is a normalized index ranging from −1 to +1. If signals X and Y have similar morphology, they will have more concordant sample pairs, and ASCI(X,Y) will approach +1. On the other hand, if signals X and Y have different morphology, they will have fewer concordant sample pairs, and ASCI(X,Y) will be less. If most sample pairs of X and Y are discordant, then ASCI(X,Y) will approach −1. However, ASCI is advantageous compared to PCC due to at least three reasons:

First, the calculation of PCC requires extensive floating-point operation including multiplication, division, and square root. On the other hand, the calculation of ASCI only requires comparison and summation. The threshold vectors that are used to define subspaces can be automatically determined from the template signal, through simple operations such as scaling (bit shifting), adding/subtracting, thresholding, etc. The normalization operation (divided by L) can be omitted because the total number of samples (L) is a known constant. For the purpose of sense event classification in implantable cardiac devices, the ASCI will be mainly used for comparison with predefined or user-programmable threshold to determine if two IEGM signals have similar morphology. In this case, the threshold can be defined in the form of X-out-of-Y criterion, or by means of bit shifting operation (e.g., to obtain L/2, 3L/4, 7L/8, etc.). Therefore, the calculation of ASCI is computationally much more efficient, and can be easily implemented in firmware or hardware of the implantable cardiac device.

Second, PCC is a parametric measure of linear relationship, and it does not account for the amplitude difference between signals. On the other hand, the calculation of ASCI takes amplitude information into consideration. For the examples shown in FIG. 5 where the subspaces are defined by four threshold vectors which are adaptive to the template signal X, a high ASCI(X,Y) value requires X and Y must stay close and have similar amplitude throughout the signal length (i.e., Y must be bounded by proximal upper and lower threshold vectors around X); otherwise, low ASCI(X,Y) value is obtained.

Thirdly, PCC is affected by each sample amplitude of each signal, thus is sensitive to additive noise such as impulse noise or continuous random noise, as well as sensitive to slight yet normal signal variation. On the other hand, the ASCI(X,Y) is calculated based on trichotomized signals TX and TY, and signal trichotomization is further based on subspaces $R_P$, $R_Z$, and $R_N$ that are adaptive to the template signal. Different means to define these subspaces can provide different degrees of tolerance of signal variation. Thus a noise-free signal and the same signal added with noise could have identical trichotomized vectors. Therefore, by properly designing subspaces according to specific application and/or prior knowledge of the signal, the ASCI can be more tolerant to additive noise and normal signal variation than PCC.

Ectopic Beat Detection

As described above, initial classification of a sense event in the implantable cardiac device can be made based on event timing information. However, misclassification between normal beat and ectopic beat may occur. For example, an AS outside the ARP may represent a normal intrinsic depolarization, or an atrial extra-systole (AES). In another example, an AS inside the ARP that is followed by a VS may also be a normal intrinsic depolarization, or an AES. Yet in another example, a VS outside the VRP may represent an antegrade conducted ventricular depolarization, or a ventricular extra-systole (VES). To improve the classification accuracy, the ASCI-based morphological analysis can be used to facilitate the ectopic beat detection in implantable cardiac devices.

Figure 6:
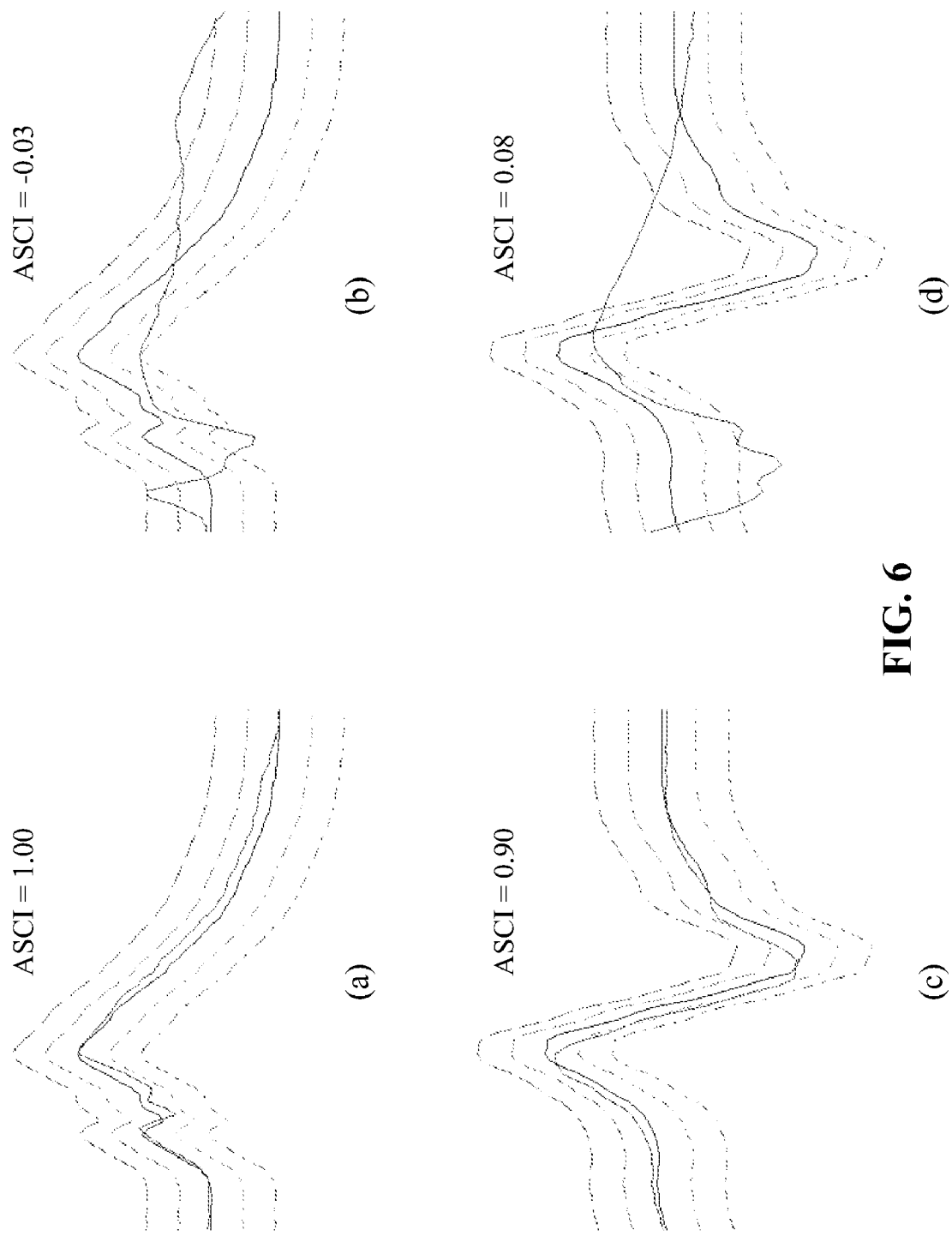
FIG. 6 shows four examples of calculating ASCI for particular application to atrial and ventricular ectopic beat detection in an implantable cardiac device.

Now refer to FIG. 6, which shows four examples of calculating ASCI for particular application to ectopic beat detection in an implantable cardiac device. In these examples, traces labeled with B are the template signals representing the normal AS template (panel (a) and panel (b)) or the normal VS template (panel (c) and panel (d)), and the traces labeled with R are the test AEGM signals corresponding to AS events (panel (a) and panel (b) or the test VEGM signals corresponding to VS events (panel (c) and panel (d)). All template signals and the test signals are aligned based on predefined fiducial points as described above.

In each plot, the four threshold vectors are defined based on the corresponding template signal according to the method illustrated in FIG. 5. Then the test signal is trichotomized, and the corresponding ASCI values are calculated. In panel (a), the calculated ASCI is 1.00, whereas in panel (b), the resulting ASCI is −0.03. Assuming a predefined ASCI threshold of 0.50, then the supra-threshold ASCI obtained in panel (a) indicates the test AEGM has similar morphology as the normal AS template, thus indicating a normal intrinsic AS event. Contrarily, the sub-threshold ASCI obtained in panel (b) indicates the test AEGM has different morphology than the normal AS template, thus indicating an AES event. In panel (c), the calculated ASCI is 0.90, whereas in panel (d), the resulting ASCI is 0.08. Assuming a predefined ASCI threshold of 0.50, then the supra-threshold ASCI obtained in panel (c) indicates the test VEGM has similar morphology as the normal VS template, thus indicating a normal intrinsic VS event. Contrarily, the sub-threshold ASCI obtained in panel (d) indicates the test VEGM has different morphology than the normal VS template, thus indicating a VES event.

Preferably, the ASCI-based morphology analysis is used in conjunction with the time interval analysis for ectopic beat detection. According to one typical embodiment of the present invention, the ASCI-based morphology analysis for ectopic beat detection is only activated when the time interval analysis could not definitely differentiate normal beat from ectopic beat. For example, a VS event without a preceding AS or AP event can be classified as a VES with high confidence, thus no additional morphological analysis is necessary.

Yet according to another embodiment of the present invention, the ASCI-based morphology analysis conducts the ectopic beat detection, independent of the time interval analysis. The analysis results from both methods are combined, e.g., through fuzzy logic, to reach the final classification results.

Yet according to a further embodiment of the present invention, the ASCI-based morphology analysis could be used in conjunction with other signal processing algorithms for ectopic beat detection in devices or systems (e.g., ECG monitors, ECG Holters, etc.) involving measurement and analysis of surface ECG signals.

Retrograde P Wave Classification

Retrograde P wave represents atrial depolarization caused by retrograde AV conduction after VP or VES. As known in the art, to differentiate retrograde atrial depolarization from normal intrinsic atrial depolarization, an implantable cardiac device usually starts a PVARP window after a VP or VES event. An AS event detected outside PVARP can be classified as intrinsic AS event, whereas an AS event detected inside PVARP can be classified as retrograde AS event. However, this simple method often leads to misclassification between intrinsic AS and retrograde AS. In one example, false classification of retrograde AS to intrinsic AS may result in pacemaker mediated tachycardia in devices operating in DDD mode. In another example, false classification of intrinsic AS to retrograde AS may result in delayed or failed mode switch during atrial tachycardia.

Improved event classification algorithms have been implemented in some implantable cardiac devices. The general concept of these algorithms is that an AS event inside the PVARP is likely as an intrinsic P wave if it is followed by a VS event within a predefined time interval, whereas an AS event inside the PVARP is suspected as a retrograde AS if the interval from VP to AS is consistent over multiple cycles. However, the classification accuracy of these algorithms is still limited.

To improve the classification accuracy between intrinsic AS and retrograde AS, the ASCI-based morphological analysis can be used in implantable cardiac devices. The basic concept is that the normal intrinsic atrial depolarization generally has distinct AEGM morphology than that of the retrograde atrial depolarization, due to different atrial activation pathways. Preferably, the ASCI-based morphology analysis is used in conjunction with the time interval analysis for retrograde P wave detection.

According to this invention, for an AS detected within the PVARP, a first ASCI value is calculated by comparing the morphology of the corresponding AEGM with that of the normal AS template. If the obtained first ASCI value is greater than a predefined threshold (e.g., 0.5), then the two signals are considered to have similar morphology, thus suggesting the event is a normal intrinsic AS. Otherwise, the two signals are considered to have different morphology. In such a case, a second ASCI value is calculated by comparing the morphology of the corresponding AEGM with that of the retrograde AS template. If the obtained second ASCI value is greater than a predefined threshold (e.g., 0.5), then the two signals are considered to have similar morphology, thus suggesting the event is a retrograde AS. Otherwise, the two signals are considered to have different morphology. This suggests that the detected AS event is neither a normal intrinsic AS, nor a retrograde AS. This could happen when the detected AS event is an AES, which could be confirmed if it is followed by a VS event within a predefined time interval. Or this could happen when the detected AS event is a far-field sense or a noise sense, and in both cases, the AS event is preferably ignored by the device.

Far-Field Sense Classification

Far-field sensing in implantable cardiac devices can adversely affect arrhythmia detection and therapy. One common problem is the far-field sensing of the ventricular depolarization (R wave) in the atrial channel. Another common problem is the far-field sensing of the ventricular repolarization (T wave) in the atrial channel. In biventricular pacing devices, there are also problems of far-field sensing of right ventricular (RV) depolarization or repolarization in the left ventricular (LV) channel, or far-field sensing of LV depolarization or repolarization in the RV.

To prevent undesirable far-field sensing in one sense channel, a common method is to start a far-field blanking (FFB) window in the channel upon delivering a pace or detecting an intrinsic depolarization in other channels. The length of the FFB must be properly adjusted so that on one hand, it can cover the cross-channel far-field signal, while on the other hand, it does not blank the in-channel real activation signal. However, the FFB adjustment may not be always effective. In some circumstances, the far-field signal may fall outside the FFB window, causing false classification of the sense event. In other circumstances, intrinsic depolarization may occur inside the FFB window. This could happen due to extrasystole, or due to sub-threshold pacing in the channel that does not capture the chamber.

To improve the classification accuracy of the far-field sense, the ASCI-based morphological analysis can be used in implantable cardiac devices. The basic concept is that the intrinsic cardiac depolarization generally has distinct IEGM morphology than that of the far-field sense signal. Preferably, the ASCI-based morphology analysis is used in conjunction with the time interval analysis for far-field sense classification.

According to this invention, for an AS detected within the FFB, a first ASCI value is calculated by comparing the morphology of the corresponding AEGM with that of the normal AS template. If the obtained first ASCI value is greater than a predefined threshold (e.g., 0.5), then the two signals are considered to have similar morphology, thus suggesting the event is a normal intrinsic AS. Otherwise, the two signals are considered to have different morphology. If the far-field AS event is not preceded by a VP nor a VES event, no further check of retrograde AS is needed. Otherwise (i.e., the far-field AS event is preceded by a VP or a VES event), a second ASCI value is calculated by comparing the morphology of the corresponding AEGM with that of the retrograde AS template. If the obtained second ASCI value is greater than a predefined threshold (e.g., 0.5), then the two signals are considered to have similar morphology, thus suggesting the event is a retrograde AS. Otherwise, the two signals are considered to have different morphology. This suggests that the detected AS event is neither a normal intrinsic AS, nor a retrograde AS. This could happen when the detected AS event is an AES, which could be confirmed if it is followed by a VS event within a predefined time interval. Or this could happen when the detected AS event is a far-field sense or a noise sense, and in both cases, the AS event is preferably ignored by the device.

Also according to this invention, a normal RV sense template and a normal LV sense template are respectively constructed and maintained in a biventricular pacing device. For an RV sense detected within the FFB of a preceding LV event, an ASCI value is calculated by comparing the morphology of the corresponding RV IEGM with that of the normal RV sense template. If the obtained ASCI value is greater than a predefined threshold (e.g., 0.5), then the two signals are considered to have similar morphology, thus suggesting the event is a normal intrinsic RV sense. Otherwise, the two signals are considered to have different morphology. This could happen when the detected RV sense event is a VES, or a far-field sense, or a noise sense, and in all these cases, the RV sense event is preferably ignored by the device. Evidently, similar event classification can be conducted for an LV sense detected within the FFB of a preceding RV event.

What is claimed is:

1. A method for classifying sense events in implantable devices using signals provided by an electrogram comprising:
   providing a template signal and a test signal from
      an intracardiac electrogram IEGM signal,
      an atrial electrogram AEGM signal,
      a ventricular electrogram VEGM signal,
      a surface electrocardiogram ECG signal, or
      a subcutaneous electrogram signal,
      the template signal and the test signal comprising samples having sample values;
   constructing at least one of
      a normal atrial sense AS template waveform from the AEGM signal that corresponds to normal intrinsic atrial depolarization;
      a normal ventricular sense VS template waveform from the VEGM signal that corresponds to antegrade conducted ventricular depolarization;
      a retrograde AS template waveform from the AEGM signal that corresponds to retrograde atrial depolarization;
      a normal right ventricular RV sense template that corresponds to normal intrinsic RV depolarization;
      a normal left ventricular LV sense template that corresponds to normal intrinsic LV depolarization;
   transforming at least the test signal into a representation of the test signal wherein the sample values of the test signal are integers;
   determining a correlation between the template signal and the test signal;
   differentiating the retrograde atrial depolarization from normal intrinsic atrial depolarization via said correlation by
      calculating for an AS event detected within a post-ventricular atrial refractory period PVARP a first correlation value by comparing a corresponding AEGM signal with the normal atrial sense AS template waveform;
      depending on the first correlation value, indicating the AS event as a normal intrinsic AS, or not, then calculating a second correlation value by comparing the corresponding AEGM signal with the retrograde AS template waveform; and,
      depending on the second correlation value indicating the AS event as a retrograde AS, or neither the normal intrinsic AS, nor the retrograde AS; and,
   classifying a sense event based on the correlation.

2. The method according to claim 1, wherein
   constructing the normal atrial sense AS template waveform comprises using the AEGM signal corresponding to at least one AS event detected outside an atrial refractory period ARP;
   constructing the normal ventricular sense VS template waveform comprises using the VEGM signal corresponding to at least one VS event detected outside a ventricular refractory period VRP and is associated with at least one preceding AS event or at least one atrial pace AP event; and, constructing the retrograde AS template waveform comprises using the AEGM signal corresponding to at least one retrograde AS event.

3. The method according to claim 2, wherein the at least one retrograde AS event is confirmed by relatively stable intervals from ventricular paces VP to refractory atrial senses.

4. The method according to claim 1, wherein constructing each type of sense template waveform comprises:
   exposing the sense event;
   collecting multiple cycles of the IEGM signal containing the sense event;
   aligning the IEGM signal based on at least one predefined fiducial point; and,
   creating a sense template waveform by averaging similar aligned IEGM cycles.

5. The method according to claim 1, where said providing the template signal comprises obtaining the template signal by averaging a plurality of cycles of signals.

6. The method according to claim 1, further comprising updating the template signal periodically or continuously after an initial template setup.

7. The method according to claim 1, further comprising aligning the template signal and test signal based on at least one predefined fiducial point.

8. The method according to claim 1, further comprising:
   associating the template signal with at least two subspaces of template signal space; and,
   transforming at least one of the template signal and the test signal with respect to the at least two subspaces.

9. The method according to claim 8, wherein the at least two subspaces are defined by
   a first subspace comprising values which differ from template signal values at most by a predefined first value; and,
   a second subspace comprising values which differ from the template signal values at least by the predefined first value.

10. The method according to claim 8, wherein the at least two subspaces comprise three subspaces and the three subspaces are defined by
    a first subspace comprising values which differ from template signal values at most by a predefined first value,
    a second subspace comprising values which differ from template signal values at least by the predefined first value and at the most by a predefined second value; and,
    a third subspace comprising values which differ from the template signal values at least by the predefined second value.

11. The method according to claim 8, wherein the at least two subspaces are bounded by threshold vectors.

12. The method according to claim 11, wherein the threshold vectors are obtained by increasing or decreasing the sample values of the template signal by a predefined fixed value, or by a predefined ratio, or by a combination of the predefined fixed value and a predefined ratio.

13. The method according to claim 8, wherein said transforming comprises assigning a first, second or third integer to a sample of a transformed signal if a corresponding sample of the template signal and/or test signal belongs to a first, second or third subspace.

14. The method according to claim 13, where the first integer is 1, the second integer is 0 and the third integer is −1.

15. The method according to claim 1, wherein said determining the correlation is performed using at least a transformed test signal.

16. The method according to claim 15, wherein said determining the correlation is performed using only the transformed test signal.

17. The method according to claim 1, wherein said determining the correlation comprises using an adapted signed correlation index that is determined by summing the sample values of a transformed test signal or by dividing a sum of the sample values of the transformed test signal by a number of samples.

18. The method according to claim 1, further comprising detecting ectopic beat events by calculating the correlation between the template signal and the test signal.

19. The method according to claim 18, wherein said detecting ectopic beat events comprises:
    determining a correlation between a normal AS template and a test AEGM signal; and,
    depending on the correlation value, indicating a normal intrinsic AS event or an atrial extra-systole AES event.

20. The method according to claim 18, wherein said detecting ectopic beat events comprises:
    determining a correlation between a normal VS template and a test VEGM signal; and,
    depending on the correlation value, indicating a normal intrinsic VS template or an ventricular extra-systole VES event.

21. The method according to claim 18, wherein said detecting ectopic beat events comprises combining with at least one of
    a time interval analysis; and/or,
    signal processing algorithms for ectopic beat detection in devices or systems involving measurement and analysis of surface ECG signals.

22. The method according to claim 21, wherein said detecting ectopic beat events is only activated when the time interval analysis cannot definitely differentiate normal beat from ectopic beat.

23. The method according to claim 1, wherein said differentiating the retrograde atrial depolarization from normal intrinsic atrial depolarization further comprises combining with a time interval analysis.

24. The method according to claim 1, further comprising ignoring the AS event if the AS event is indicated as neither the normal intrinsic AS, nor the retrograde AS.

25. A method for classifying sense events in implantable devices using signals provided by an electrogram comprising:
    providing a template signal and a test signal, the template signal and the test signal comprising samples having sample values;
    transforming at least the test signal into a representation of the test signal wherein the sample values of the test signal are integers;
    determining a correlation between the template signal and the test signal;
    classifying a sense event based on the correlation;
    performing far field sensing classification with the correlation;
    calculating for an AS event detected within a far-field blanking FFB window a first correlation value by comparing a corresponding AEGM signal with a normal atrial sense AS template waveform;
    depending on the first correlation value, indicating the AS event as a normal intrinsic AS, or not, then further checking whether the AS event detected within the FFB is preceded by a VP or a VES event;

depending on the result of the checking, calculating a second correlation value by comparing the corresponding AEGM signal with a retrograde AS template; and depending on the second correlation value, indicating the AS event as a retrograde AS, or neither a normal intrinsic AS, nor a retrograde AS.

26. The method according to claim 25, wherein said performing said far field sensing classification comprises combining with a time interval analysis.

27. The method according to claim 25, where the AS event in FFB is ignored if the AS event is not preceded by the VP nor the VES event.

28. The method according to claim 25, where the AS event in FFB is ignored if the AS event is indicated as neither the normal intrinsic AS, nor the retrograde AS.

29. The method according to claim 25, further comprising:

calculating a correlation value for an RV sense event detected within the FFB of a preceding LV event by comparing a corresponding RV IEGM with a normal RV sense template and depending on the correlation value, indicating the RV sense event as a normal intrinsic RV sense or a VES, a far-field sense, or a noise sense; and/or, calculating a correlation value for an LV sense event detected within the FFB of a preceding RV event by comparing a corresponding LV IEGM with a normal LV sense template and depending from the correlation value indicating the LV sense event as a normal intrinsic LV sense or the VES, the far-field sense, or the noise sense.

30. The method according to claim 29, wherein the RV sense event or the LV sense event in respective FFB is ignored if it is indicated as the VES, the far-field sense, or the noise sense.

31. A computer-readable storage medium comprising program code that causes a data processing device to classify sense events in implantable devices through use of signals obtained from an electrogram, wherein said program code is configured to:

provide a template signal and a test signal, the template signal and the test signal comprising samples having sample values;

transform at least the test signal into a representation of the test signal wherein the sample values of the test signal are integers;

determine a correlation between the template signal and the test signal;

perform far field sensing classification with the correlation;

calculate for an AS event detected within a far-field blanking FFB window a first correlation value by comparison of a corresponding AEGM signal with a normal atrial sense AS template waveform;

and depending on the first correlation value, indicate the AS event as a normal intrinsic AS, or not, then further check whether the AS event detected within the FFB is preceded by a VP or a VES event;

and depending on the result of the check, calculate a second correlation value by comparison of the corresponding AEGM signal with a retrograde AS template;

and depending on the second correlation value, indicate the AS event as a retrograde AS, or neither a normal intrinsic AS, nor a retrograde AS; and, classify a sense event based on the correlation.

* * * * *